US010085774B2

(12) United States Patent
Jackson

(10) Patent No.: US 10,085,774 B2
(45) Date of Patent: *Oct. 2, 2018

(54) POLYAXIAL BONE SCREW WITH MULTI-PART SHANK RETAINER AND PRESSURE INSERT

(71) Applicant: Roger P. Jackson, Prairie Village, KS (US)

(72) Inventor: Roger P. Jackson, Prairie Village, KS (US)

(*) Notice: Subject to any disclaimer, the term of this patent is extended or adjusted under 35 U.S.C. 154(b) by 0 days.

This patent is subject to a terminal disclaimer.

(21) Appl. No.: 15/617,614

(22) Filed: Jun. 8, 2017

(65) Prior Publication Data

US 2017/0265902 A1   Sep. 21, 2017

Related U.S. Application Data

(63) Continuation of application No. 15/095,022, filed on Apr. 9, 2016, now Pat. No. 9,700,354, which is a continuation of application No. 12/930,768, filed on Jan. 14, 2011, now Pat. No. 9,320,545, which is a continuation of application No. 12/080,202, filed on Apr. 1, 2008, now Pat. No. 7,875,065, which is a continuation-in-part of application No. 11/281,818, filed on Nov. 17, 2005, now Pat. No. 7,625,396.

(60) Provisional application No. 60/630,478, filed on Nov. 23, 2004.

(51) Int. Cl.
*A61B 17/70* (2006.01)

(52) U.S. Cl.
CPC ...... *A61B 17/7035* (2013.01); *A61B 17/7032* (2013.01); *A61B 17/7037* (2013.01); *A61B 17/7011* (2013.01)

(58) Field of Classification Search
CPC ............ A61B 17/7011; A61B 17/7032; A61B 17/7037; A61B 17/7035; A61B 17/704; A61B 17/7031; A61B 17/7008; A61B 17/7002; A61B 17/7085; A61B 17/708; A61B 17/7091; A61B 17/7055
USPC ......... 606/246–279, 300–320; 411/353, 533, 411/922, 81
See application file for complete search history.

(56) References Cited

U.S. PATENT DOCUMENTS

| | | |
|---|---|---|
| 5,257,993 A | 11/1993 | Asher et al. |
| 5,545,165 A | 8/1996 | Biedermann et al. |
| 5,716,356 A | 2/1998 | Biedermann et al. |
| 5,720,751 A | 2/1998 | Jackson |

(Continued)

OTHER PUBLICATIONS

International Search Report and Written Opinion PCT/US2015/056706, dated Jan. 6, 2016.

(Continued)

*Primary Examiner* — Pedro Philogene
(74) *Attorney, Agent, or Firm* — Polsinelli PC

(57) ABSTRACT

A polyaxial bone screw assembly includes a threaded shank body having an upper portion, a receiver, a compression insert and an articulation structure made from at least two discrete pieces. The shank upper portion cooperates with the compression insert to place the retainer in frictional engagement with the receiver. The geometry of the retainer structure pieces corresponds and cooperates with the external geometry of the shank upper portion to frictionally envelope the retainer structure between the capture structure and an internal surface defining a cavity of the receiver.

12 Claims, 5 Drawing Sheets

(56) References Cited

U.S. PATENT DOCUMENTS

| | | |
|---|---|---|
| 5,873,878 A | 2/1999 | Harms et al. |
| 5,910,141 A | 6/1999 | Morrison et al. |
| 6,077,262 A | 6/2000 | Schlapfer et al. |
| 6,440,133 B1 | 8/2002 | Beale et al. |
| 6,648,888 B1 | 11/2003 | Shluzas |
| 6,660,006 B2 | 12/2003 | Markworth et al. |
| 6,905,500 B2 | 6/2005 | Jeon et al. |
| 7,179,261 B2 | 2/2007 | Sicvol et al. |
| 7,250,052 B2 | 7/2007 | Landry et al. |
| 7,476,228 B2 | 1/2009 | Abdou |
| 7,559,943 B2 * | 7/2009 | Mujwid ............ A61B 17/7032 606/266 |
| 7,618,440 B2 | 11/2009 | Gray et al. |
| 7,618,444 B2 | 11/2009 | Shluzas |
| 7,625,396 B2 * | 12/2009 | Jackson ............ A61B 17/7037 606/266 |
| 7,641,670 B2 | 1/2010 | Davison et al. |
| 7,736,305 B2 | 6/2010 | DiPoto |
| 7,776,040 B2 | 8/2010 | Markworth et al. |
| 7,815,650 B2 | 10/2010 | Shluzas et al. |
| 7,862,587 B2 | 1/2011 | Jackson |
| 7,875,065 B2 * | 1/2011 | Jackson ............ A61B 17/7035 606/266 |
| 7,887,539 B2 | 2/2011 | Dunbar et al. |
| 7,955,355 B2 | 6/2011 | Chin |
| 7,985,242 B2 | 7/2011 | Forton et al. |
| 8,002,798 B2 | 8/2011 | Chin et al. |
| 8,034,089 B2 * | 10/2011 | Matthis ............ A61B 17/7037 606/306 |
| 8,105,361 B2 | 1/2012 | Anderson et al. |
| 8,273,089 B2 | 9/2012 | Jackson |
| 8,308,782 B2 * | 11/2012 | Jackson ............ A61B 17/7008 606/305 |
| 8,709,051 B2 | 4/2014 | Hammer et al. |
| 9,320,545 B2 * | 4/2016 | Jackson ............ A61B 17/7035 |
| 9,522,021 B2 | 12/2016 | Jackson |
| 9,700,354 B2 * | 7/2017 | Jackson ............ A61B 17/7032 |
| 2002/0161368 A1 | 10/2002 | Foley et al. |
| 2003/0158552 A1 * | 8/2003 | Jeon ................ A61B 17/7037 606/270 |
| 2005/0065517 A1 | 3/2005 | Chin |
| 2005/0192589 A1 | 9/2005 | Raymond et al. |
| 2005/0277928 A1 * | 12/2005 | Boschert ............ A61B 17/7037 606/328 |
| 2008/0009864 A1 | 1/2008 | Forton et al. |
| 2008/0077139 A1 | 3/2008 | Landry et al. |
| 2012/0277800 A1 | 6/2012 | Jackson |
| 2014/0031873 A1 | 1/2014 | Jackson |
| 2016/0302835 A1 | 10/2016 | Jackson |

OTHER PUBLICATIONS

International Preliminary Report on Patentability regarding PCT/US2015/056703, dated Nov. 17, 2016.

* cited by examiner

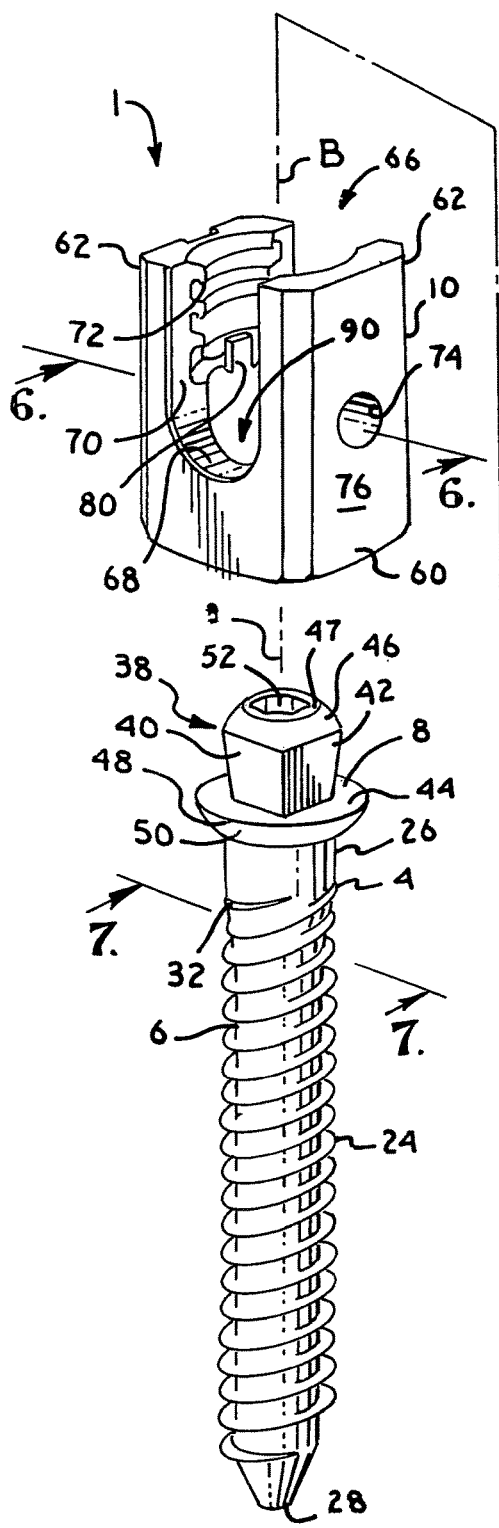
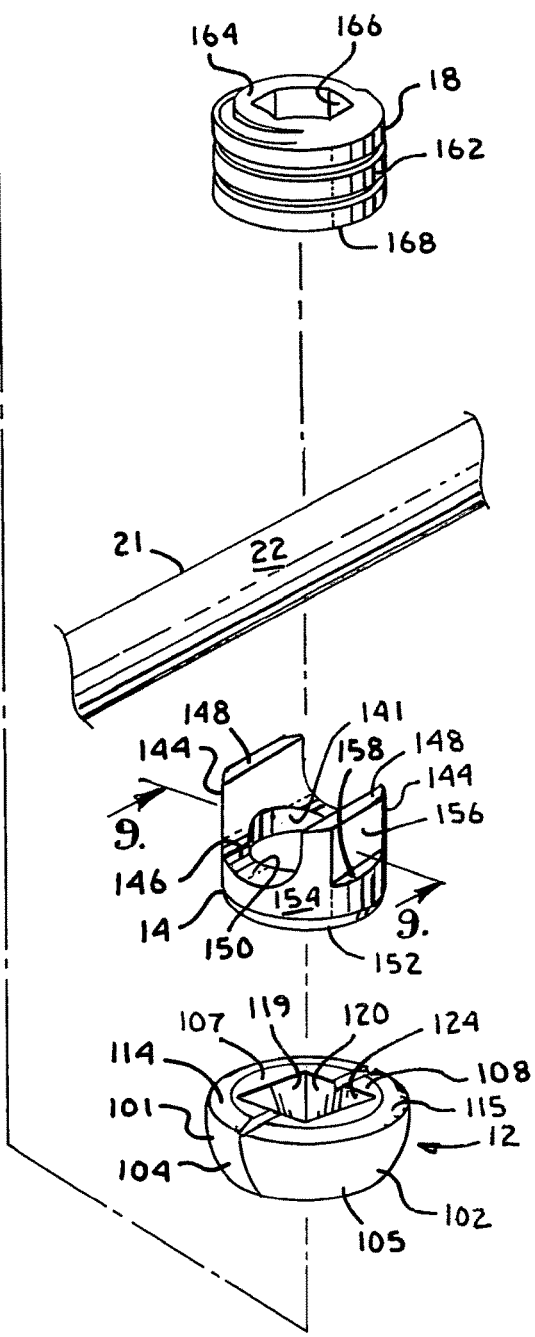
Fig. 1.

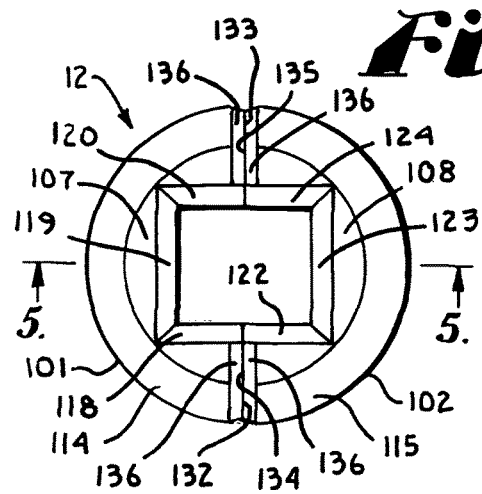
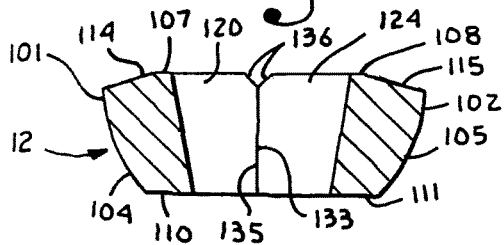
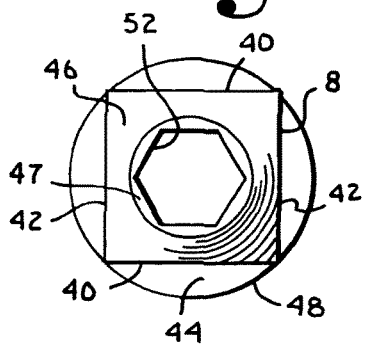
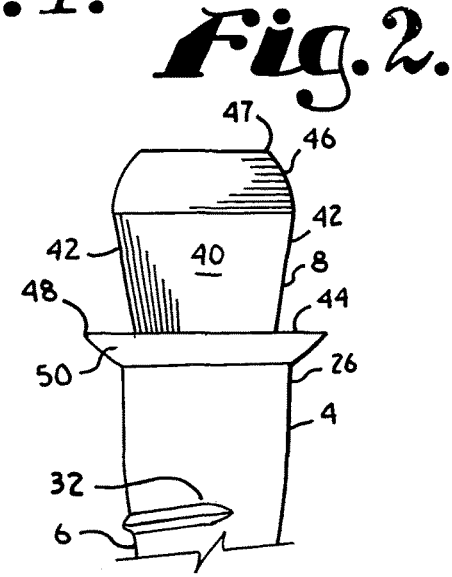
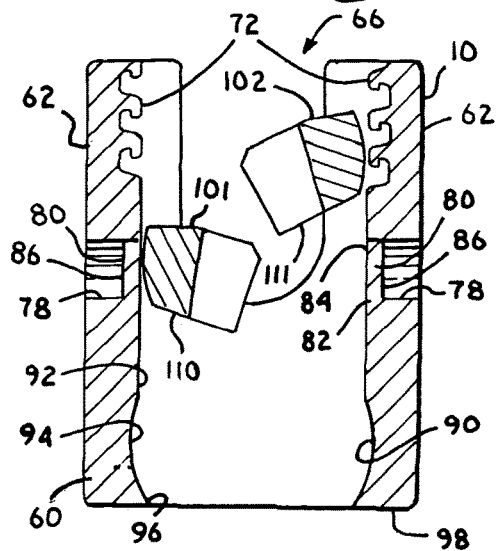

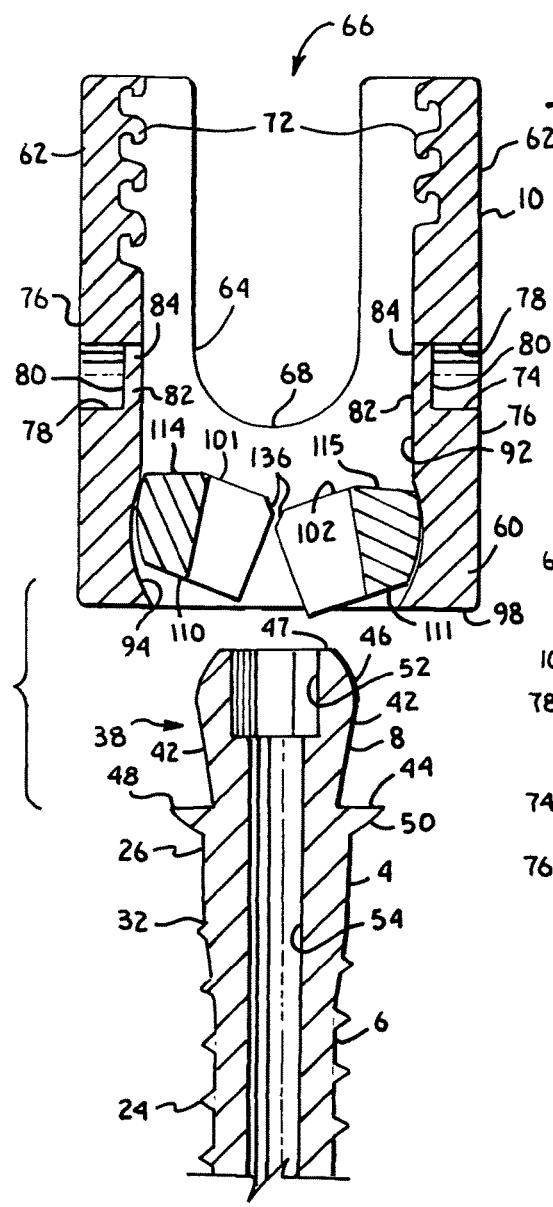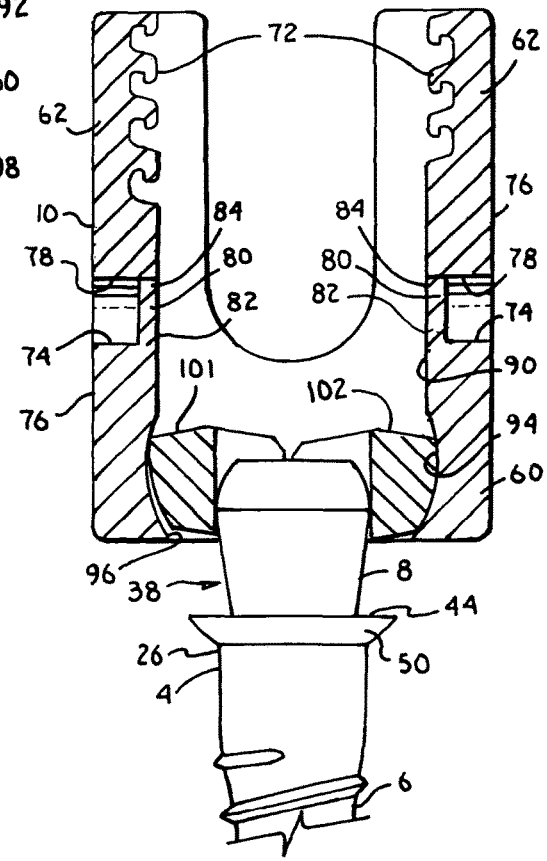

POLYAXIAL BONE SCREW WITH MULTI-PART SHANK RETAINER AND PRESSURE INSERT

CROSS-REFERENCE TO RELATED APPLICATIONS

This application is a continuation of U.S. patent application Ser. No. 12/080,202, filed Apr. 1, 2008 that was a continuation-in-part of U.S. patent application Ser. No. 11/281,818 filed Nov. 17, 2005, now U.S. Pat. No. 7,625,396, issued Dec. 1, 2009 that claimed the benefit of U.S. Provisional Application No. 60/630,478 filed Nov. 23, 2004, all of which are incorporated by reference herein.

BACKGROUND OF THE INVENTION

The present invention is directed to polyaxial bone screws for use in bone surgery, particularly spinal surgery and particularly to such screws that have pressure inserts.

Bone screws are utilized in many types of spinal surgery in order to secure various implants to vertebrae along the spinal column for the purpose of stabilizing and/or adjusting spinal alignment. Although both closed-ended and open-ended bone screws are known, open-ended screws are particularly well suited for connections to rods and connector arms, because such rods or arms do not need to be passed through a closed bore, but rather can be laid or urged into an open channel within a receiver or head of such a screw.

Typical open-ended bone screws include a threaded shank with a pair of parallel projecting branches or arms which form a yoke with a U-shaped slot or channel to receive a rod. Hooks and other types of connectors, as are used in spinal fixation techniques, may also include open ends for receiving rods or portions of other structure.

A common mechanism for providing vertebral support is to implant bone screws into certain bones which then in turn support a longitudinal structure such as a rod, or are supported by such a rod. Bone screws of this type may have a fixed head or receiver relative to a shank thereof. In the fixed bone screws, the rod receiver head cannot be moved relative to the shank and the rod must be favorably positioned in order for it to be placed within the receiver head. This is sometimes very difficult or impossible to do. Therefore, polyaxial bone screws are commonly preferred.

Open-ended polyaxial bone screws allow rotation of the head or receiver about the shank until a desired rotational position of the head is achieved relative to the shank. Thereafter, a rod can be inserted into the head or receiver and eventually the receiver is locked or fixed in a particular position relative to the shank. During the rod implantation process it is desirable to utilize bone screws or other bone anchors that have components, or inserts that remain within the bone screw and further remain properly aligned during what is sometimes a very lengthy, difficult procedure.

SUMMARY OF THE INVENTION

A polyaxial bone screw assembly according to the invention includes a shank having an upper portion and a body for fixation to a bone; a head or receiver defining an open channel; a multi-part or piece retainer for pivotally holding the upper portion in the receiver; and at least one compression insert spaced above and apart from the retainer structure. The shank upper portion is bottom or up-loadable into the receiver, cooperates with the retainer, and has a top end which extends above a top surface of the retainer; the retainer having polyaxial motion with respect to the receiver; and the retainer including more than one discrete piece, each piece frictionally engageable with the shank upper portion, slidably engageable with the receiver and located between the shank upper portion and the receiver and spaced below the insert. In embodiments wherein the compression insert includes arms defining a U-shaped channel, the receiver further includes structure cooperating with the compression insert that hold such insert in a desired position or alignment within the receiver, such as spring tabs that project into the receiver cavity either upwardly or downwardly and into depressions or grooves formed in the insert arms.

OBJECTS AND ADVANTAGES OF THE INVENTION

Therefore, it is an object of the present invention to provide apparatus and methods directed to a shank that is up or down loadable into a cavity in a receiver of the screw and that utilizes a retainer that may be also uploaded or downloaded into the cavity. Another object of the invention is to provide discrete retainer parts or segments configured to fixedly engage the shank upper portion and slidably engage the receiver so as to polyaxially articulate with the receiver until the receiver is fixed relative to the shank, when a desired configuration is acquired, while therebetween holding the shank upper portion in a spaced relation from the receiver. Furthermore, it is an object of the invention to provide a lightweight, low profile polyaxial bone screw that assembles in such a manner that the components cooperate to create an overall structure that provides an even gripping of a shank capture structure to the receiver. Furthermore, it is an object of the invention to provide apparatus and methods that are easy to use and especially adapted for the intended use thereof and wherein the tools are comparatively inexpensive to produce.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an exploded perspective view of a polyaxial bone screw assembly according to the present invention including a shank, a receiver, a two-piece retainer and a compression insert and further shown with a longitudinal connecting member and a closure top.

FIG. 2 is an enlarged and partial front elevational view of the shank of FIG. 1.

FIG. 3 is an enlarged top plan view of the shank of FIG. 1.

FIG. 4 is an enlarged top plan view of the retainer of FIG. 1.

FIG. 5 is an enlarged cross-sectional view taken along the line 5-5 of FIG. 4.

FIG. 6 is an enlarged cross-sectional view of the receiver, taken along the line 6-6 of FIG. 1 and the two-piece retainer as shown in the cross-sectional view of FIG. 5 in a method of assembly according to the invention.

FIG. 7 is an enlarged cross-sectional view of the receiver, taken along the line 6-6 of FIG. 1, an enlarged and partial cross-sectional view of the shank, taken along the line 7-7 of FIG. 1, and shown with the two-piece retainer shown in cross-section as in FIG. 5 in an early assembly step according to the invention.

FIG. 8 is an enlarged cross-sectional view of the receiver, taken along the line 6-6 of FIG. 1, a partial front elevational view of the shank of FIG. 1, and shown with the two-piece retainer shown in cross-section as in FIG. 5 in an intermediate assembly step.

DETAILED DESCRIPTION OF THE INVENTION

Figure 9:
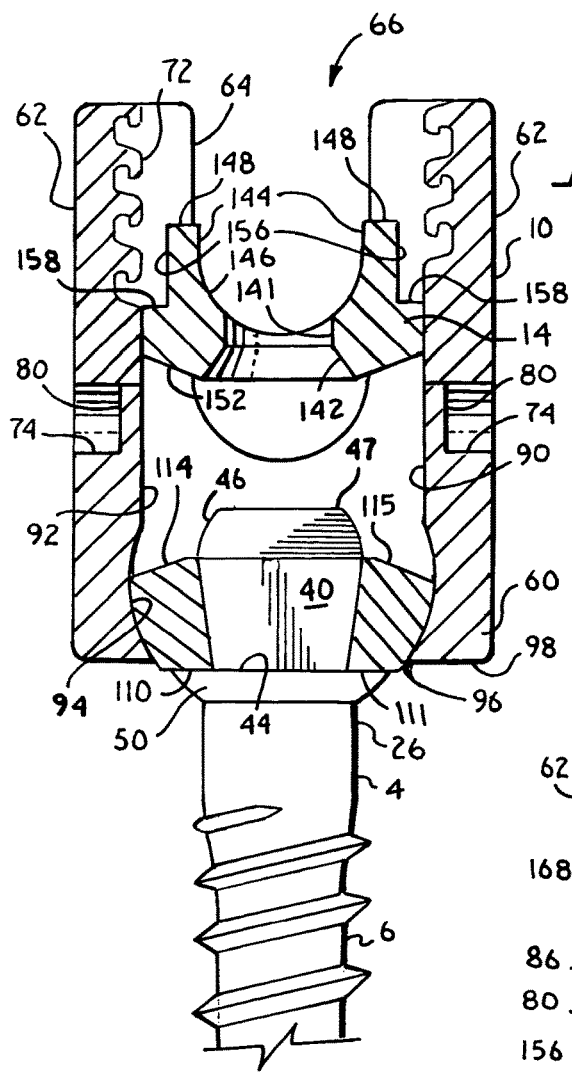
FIG. 9 is an enlarged cross-sectional view of the receiver, taken along the line 6-6 of FIG. 1, a partial front elevational view of the shank of FIG. 1, shown with the two-piece retainer shown in cross-section as in FIG. 5 being assembled with the shank, and a cross-sectional view of the compression insert taken along the line 9-9 of FIG. 1 in an initial assembly step within the receiver.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the bone attachment structures in actual use.

With reference to FIGS. 1-11 the reference number 1 generally represents a polyaxial bone screw apparatus or assembly according to the present invention. The assembly 1 includes a shank 4, that further includes a body 6 integral with an upwardly extending upper portion or capture structure 8 having a top end surface 46; a receiver 10; a two-piece or part retainer structure 12 and a compression or pressure insert 14. The shank 4, receiver 10, retainer structure 12 and pressure insert 14 preferably are assembled prior to implantation of the shank body 6 into a vertebra (not shown).

FIG. 1 further shows a closure structure 18 of the invention for biasing a longitudinal member such as a rod 21 against the pressure insert 14 which engages the shank top end surface 46 and biases the lower retainer structure 12 into fixed frictional contact with both the shank upper portion 8 and the receiver 10, so as to fix the longitudinal connecting member 21 relative to the vertebra. The shank top end 46 is spaced above the retainer 12 and the retainer 12 is disposed between the shank upper portion 8 and the receiver 10 lower portion 60. The receiver 10 and the shank 4 cooperate in such a manner that the receiver 10 and the shank 4 can be secured at any of a plurality of angles, articulations or rotational alignments relative to one another and within a selected range of angles both from side to side and from front to rear, to enable flexible or articulated engagement of the receiver 10 with the shank 4 until both are locked or fixed relative to each other near the end of an implantation procedure.

The shank 4, best illustrated in FIGS. 1, 2, 3 and 7, is elongate, with the shank body 6 having a helically wound bone implantable thread 24 extending from near a neck 26 located adjacent to the upper portion or capture structure 8, to a tip 28 of the body 6 and extending radially outwardly therefrom. During use, the body 6 utilizing the thread 24 for gripping and advancement is implanted into a vertebra leading with the tip 28 and driven down into the vertebra with an installation or driving tool (not shown), so as to be implanted in the vertebra to near the neck 26, as more fully described in the paragraphs below. The shank 4 has an elongate axis of rotation generally identified by the reference letter A.

The neck 26 extends axially outward and upward from the shank body 6. The neck 26 may be of slightly reduced radius as compared to an adjacent upper end or top 32 of the body 6 where the thread 24 terminates. Further extending axially and outwardly from the neck 26 is the shank upper portion 8 that provides a connective or capture apparatus disposed at a distance from the upper end 32 and thus at a distance from a vertebra when the body 6 is implanted in such vertebra.

The shank upper portion or capture structure 8 is configured for connecting the shank 4 to the receiver 10 and capturing the shank upper portion structure in the receiver 10. In the embodiment shown, the structure 8 includes a polyhedral formation, specifically a polyhedron-like structure, generally 38, having a first pair of opposed oblique surfaces 40 and a second pair of adjacent opposed oblique surfaces 42, each of the surfaces 40 and 42 are generally in the shape of an inverted isosceles trapezoid and extend from an annular seating surface 44 to an upper end or top curved surface 46. The top surface 46 is substantially spherical or domed shaped and terminates at a narrow top annular surface 47 that is perpendicular to the axis A. The annular surface 44 is also substantially perpendicular to the axis A and the surfaces 40 and 42 form an oblique angle with respect to the surface 44. The optional annular seating surface 44 partially defines a ledge having a rim 48 and a substantially spherical lower surface 50 that extends from the rim 48 to adjacent the neck 26. The term oblique is used herein to describe the surfaces 40 and 42 that are slanted or inclined in direction or course or position neither parallel nor perpendicular nor right-angular, with respect to the shank body 6, but otherwise may be disposed at a variety of angles with respect to the axis A. Also, other geometries are possible (e.g., conical). The oblique surfaces 40 and 42 slope from the top surface 46 toward the axis A in a direction toward the tip 28 of the shank body 6. A width of each of the surfaces 40 and 42 adjacent to the seating surface 44 is smaller than a width of each of the surfaces 40 and 42 measured near the spherical surface 46.

The shank 4 further includes a tool engagement structure or inner drive 52 formed in the surface 47. The illustrated drive 52 is a hex drive or aperture for engaging a hex-shaped driving tool (not shown) for both driving and rotating the shank body 6 into a vertebra. Other shaped drives and cooperating tools are possible, such as grooved, multi-lobular, etc. While not required in accordance with practice of the invention, the surfaces 40, 42, 44 and 46 may be scored or knurled to further increase frictional engagement between such surfaces and cooperating surfaces of the retainer 12 and insert 14.

The shank 4 shown in the drawings is cannulated, having a small central bore 54 extending an entire length of the shank 4 along the axis A from the internal drive 52 to the tip 28. The bore 54 is coaxial with the threaded body 6. The bore 54 provides a passage through the shank 4 interior for a length of wire (not shown) inserted into a vertebra prior to the insertion of the shank body 6, the wire providing a guide for insertion of the shank body 6 into the vertebra 15.

To provide a biologically active interface with the bone, the threaded shank body 6 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate ($Ca_3(PO_4)_2$), tetra-calcium phosphate ($Ca_4P_2O_9$), amorphous calcium phosphate and hydroxyapatite ($Ca_{10}(PO_4)_6(OH)_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding.

Figure 10:
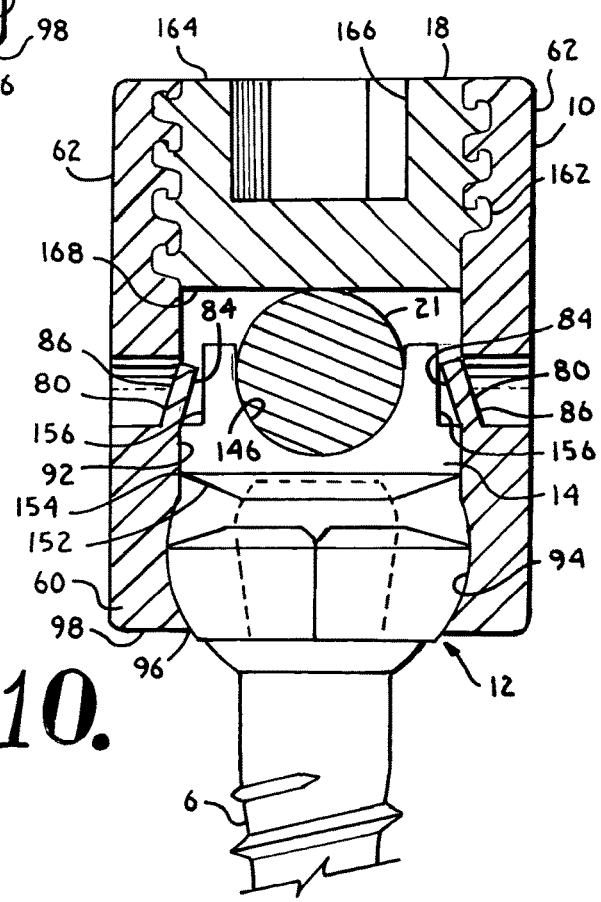
FIG. 10 is an enlarged cross-sectional view of the receiver, taken along the line 6-6 of FIG. 1, a partial front elevational view of the shank of FIG. 1 with hidden portions shown in phantom, shown assembled with the two-piece retainer of FIG. 1 in front elevation and the compression insert of FIG. 1 in front elevational and further shown with the longitudinal connecting member and closure top of FIG. 1 with portions broken away to show the detail thereof.
Figure 11:
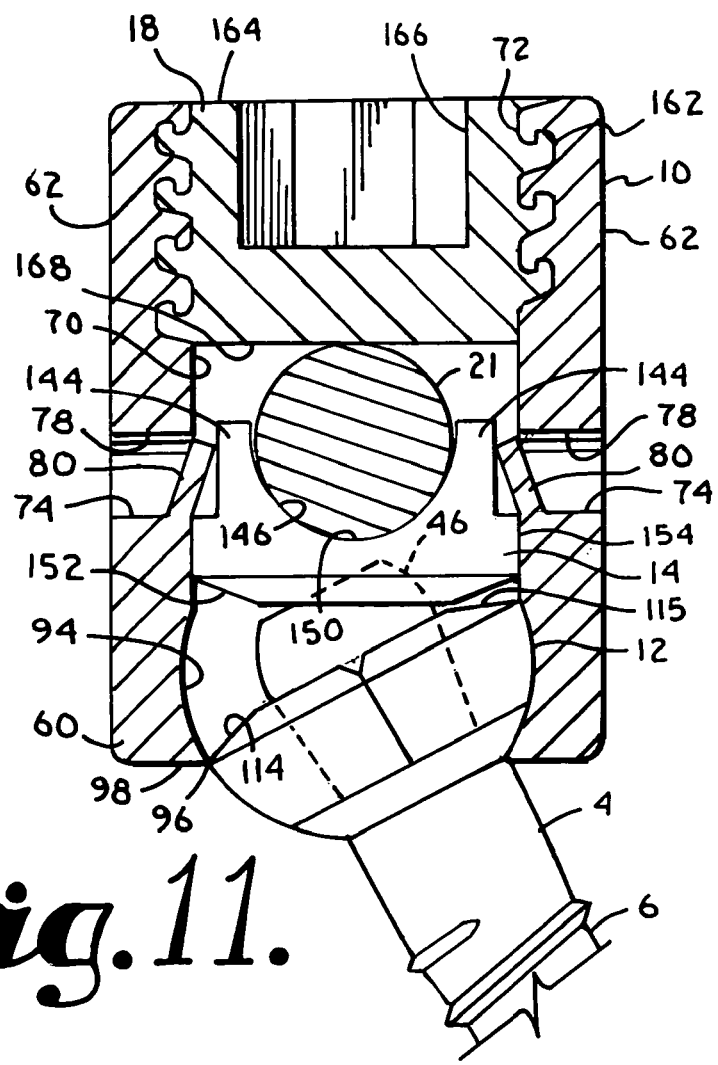
FIG. 11 is an enlarged and partial view similar to FIG. 10 further showing a rotational extent of the shank and cooperating two-piece retainer.

With particular reference to FIGS. 1 and 6-11, the receiver 10 has a generally U-shaped appearance with a discontinuous partially cylindrical and partially spherical inner profile and a partially curved and partially faceted outer profile. The receiver has an axis of rotation B that is shown in FIG. 1 as being aligned with and the same as the axis of rotation A of the shank 4, such orientation being desirable during assembly of the receiver 10 with the shank 4, the retainer pieces 12 and the insert 14. After the receiver 10 is pivotally attached to the shank 4, and the assembly 1 is implanted in a vertebra (not shown), the axis B is typically disposed at an angle with respect to the axis A as shown in FIG. 11.

The receiver 10 includes a base 60 integral with a pair of opposed upstanding arms 62 forming a cradle and defining a U-shaped channel 64 between the arms 62 with an upper opening, generally 66, and a lower seat 68, the channel 64 having a width for operably snugly receiving the rod 21 between the arms 62. Each of the arms 62 has an interior surface 70 that defines the inner cylindrical profile and includes a partial helically wound guide and advancement structure 72. In the illustrated embodiment, the guide and advancement structure 72 is a partial helically wound interlocking flangeform configured to mate under rotation with a similar structure on the closure structure 18, as described more fully below. However, it is foreseen that the guide and advancement structure 72 could alternatively be a square-shaped thread, a buttress thread, a reverse angle thread or other thread like or non-thread like helically wound discontinuous advancement structure for operably guiding under rotation and advancing the closure structure 18 downward between the arms 62, as well as eventual torquing when the closure structure 18 abuts against the rod 21, or in some embodiments, an upper compression insert.

An opposed pair of tool receiving and engaging apertures 74 are formed on outer surfaces 76 of the arms 62. A pair of substantially cylindrical inner surfaces 78 define the apertures 74, with a portion of each of the apertures 74 extending through the arms 62 as illustrated, for example, in FIGS. 10 and 11. A pair of tabs 80, each having a lower end or body portion 82 integral with a respective arm 62 at a lower portion of one of the cylindrical surfaces 78, and an upper end portion 84 extending upwardly and, as shown in FIG. 11, also inwardly, from the respective lower body portion 82, the tab 80 generally directed towards the guide and advancement structure 72 of the respective arm 62 and also toward the axis B. An operational orientation of each of the tabs 80 is angled toward the axis B with an inner surface or edge of the upper end portion 84 in sliding engagement with a surface or slot in the cooperating insert 14 as will be described in greater detail below. The tabs 80 are typically initially disposed parallel to the axis B as shown in FIG. 6, and then a tool (not shown) is inserted into the aperture 74 from the outside surface 76 and engages and pushes a surface 86 of the tab 80 and bends the tab 80 inwardly in a direction toward the axis B until the tab 80 is at the illustrated desired angular position. Such bending of the tabs 80 may be performed either prior to or after assembly of the receiver 10 with the insert 14, the shank 4 and the retainer pieces 12. It is also foreseen that the tabs 80 may be machined or otherwise pre-fabricated to be angled or directed toward the axis B as is shown in the drawing figures. In other embodiments of the invention, the tabs may be integral with an upper portion of receiver near the aperture 74 and be directed downwardly away from the guide and advancement structures 72. The illustrated tabs 80 are resilient, having a spring-like nature. Thus, when operatively cooperating with the insert 14, the tabs 80 bias against the insert 14, holding such insert in a desired position and yet the tabs 80 are flexible enough to allow a user to make desired adjustments of the position of the insert 14 within the receiver 10.

Each of the illustrated receiver arms 62 may also include a V-shaped or undercut tool engagement groove (not shown), formed on outer surfaces 76 thereof which may be used for holding the receiver 10 with a holding tool (not shown) having projections that are received within such grooves during implantation of the shank body 6 and/or during subsequent installation of the rod 21 or other longitudinal connecting member and the closure structure 18. It is foreseen that tool receiving grooves or apertures may be configured in a variety of shapes and sizes and be disposed at other locations on the receiver arms 62.

Communicating with the U-shaped channel 64 of the receiver 10 is a chamber or cavity 90 defined in part by a substantially cylindrical upper portion 92 and by a lower inner substantially spherical retainer seating surface 94 of the base 60. The upper portion 92 is located below the guide and advancement structures 72 and may include one or more cylindrical surfaces for sliding cooperation with an insert or inserts. The apertures 74 and the tabs 80 communicate with the cylindrical upper portion 92. The seating surface 94 is near or adjacent to the cylindrical portion 92. The seating surface 94 is sized and shaped for slidable mating and eventual frictional engagement with the retainer pieces 12, as described more fully below. The cavity 90 opens into the U-shaped channel 64 and also to a lower neck 96 defining a bore or circular opening that communicates with a lower exterior 98 of the base 60. The circular neck 96 is coaxially aligned with the rotational axis B of the receiver 10. The neck 96 is sized and shaped to be smaller than an outer radial dimension of the operationally assembled retainer pieces 12, as will be discussed further below, so as to form a restriction at the location of the neck relative to the retainer 12, to prevent the retainer 12 from passing from the cavity 90 and out to the lower exterior 98 of the receiver 10 when the retainer 12 is seated and assembled about the shank upper portion 8.

The two-part retainer and articulation structure 12 is used to retain the upper portion or capture structure 8 of the shank 4 within the receiver 10 and articulate the shank body 6 with respect to the receiver 10. The retainer pieces are each sized and shaped to frictionally engage the shank upper portion while being pivotally mounted with respect to the receiver, the pieces located below the top end surface 46 and between the shank upper portion and the receiver base 60 and being articulatable with respect to the receiver surface 94 until the shank 6 is fixed in a desired position with respect to the receiver base 60. The retainer structure 12, best illustrated in FIGS. 1, 4 and 5, has an operational central axis that is the same as the elongate axis A associated with the shank 4. The structure 12 includes a first piece or part 101 and an opposingly positioned, and in this embodiment a substantially identical or mirror image second piece or part 102. The parts 101 and 102 provide a collar about the upper portion 8, with the top surface 46 of the portion 8 extending upwardly above the parts 101 and 102 and towards the opening 66 within the receiver 10, and each of the parts 101 and 102 disposed between the portion 8 and the receiver 10 when installed, as will be discussed more fully below. The parts or pieces 101 and 102 slidably and closely grip both the upper portion 8 and the seating surface 94, providing an even and uniform gripping surface between the shank 4 and the receiver 10 at the spherical seating surface 94 when force is directed onto the shank domed top surface 46 by the insert 14 cooperating with the rod 21 and the closure structure 18, or by other types of longitudinal members, inserts and closure structures.

Although a two-piece retainer structure 12 is illustrated herein, it is foreseen that the retainer structure may be made up of more than two pieces, each slidably frictionally matable with both the shank upper portion or capture structure 8 and the seating surface 94 of the receiver 10. The pieces may also be of varying sizes and not necessarily mirror images of one another. The mating surfaces of the shank upper portion and cooperating retainer pieces may have greater or fewer planar surfaces or may be curved, for example, conical in form. Additionally, it is foreseen that the pieces may include a plurality of planar or curved surfaces, such as undulating or zig-zag surfaces, forming peaks and valleys that would cooperate and mate with similarly configured surfaces on the shank upper portion. Furthermore, although the illustrated embodiment shows the parts 101 and 102 in contact with each other when fully installed in the receiver 10 and in contact with the shank upper portion 8, it is foreseen that the parts 101 and 102 may be sized and shaped so as to be in spaced relation to one another when fully installed with the shank upper portion 8 and within the receiver 10.

Each retainer part 101 and 102 includes a substantially spherical outer surface, 104 and 105, respectively, each having a radius substantially similar to a radius of the receiver seating surface 94. The parts 101 and 102 further include respective planar top surfaces 107 and 108 and respective planar bottom surfaces 110 and 111. The illustrated surface 107 and the surface 110 are substantially parallel. The illustrated surface 108 and the surface 111 are substantially parallel. The surfaces 110 and 111 each abut and seat upon the annular seating surface 44 of the shank 4 when fully installed in the receiver 10 as shown in FIGS. 9-11. Adjacent to the top surfaces 107 and 108 are respective sloping planar surfaces 114 and 115. The surface 114 is adjacent to the spherical outer surface 104 and the surface 115 is adjacent to the spherical outer surface 105. As shown in FIG. 11, for example, the surfaces 114 and 115 advantageously allow for clearance between the retainer 12 and the insert 14 when pivoting the shank 4 with respect to the receiver 10 into a desired position.

With particular reference to FIG. 2, each of the retainer structure parts 101 and 102 have a squared-off U-shape or C-shape, when viewed from the top or bottom, with planar, sloping surfaces formed about a space or passage sized and shaped to mate with the surfaces 40 and 42 of the shank upper portion 8. With particular reference to FIG. 4, the part 101 includes sloping inner planar surfaces 118, 119 and 120 and the part 102 includes adjacent inner sloping planar surfaces 122, 123 and 124. When the retainer structure parts 101 and 102 are operationally disposed in the receiver 10 with the substantially spherical surfaces 104 and 105 in frictional contact with the spherical seating surface 94, and the bottom surfaces 110 and 111 are seated on the annular seating surface 44, which in some embodiments is not needed, of the shank upper portion 8, the surfaces 118, 119, 120, 122, 123 and 124 are disposed at a degree of inclination with respect to the bottom surfaces 110 and 111, respectively, corresponding or congruent to a degree of inclination of the side surfaces 40 and 42 of the upper portion 8 with respect to the seating surface 44, such that substantially full frictional contact is made between at least one of the opposed pair surfaces 40 or 42 with the surfaces 119 and 123 of the respective parts 101 and 102 with the surfaces 118, 120, 122 and 124 being in slidable contact with the other pair of opposed surfaces 40 or 42. Once in full operational assembly and locked into place, preferably all the surfaces 118, 119, 120, 122, 123 and 124 are in full or at least partial frictional engagement with one of the surfaces 40 and 42. It is noted that because the parts 101 and 102 are substantially identical and mirror images of each other, and the surfaces 40 and 42 of the shank upper portion also are substantially identical, the retainer structure functions equally well with the sloped surfaces 118, 119, 120, 122, 123 and 124 in contact with either of the surfaces 40 and 42 of the shank upper portion 8. Although the illustrated walls or surfaces 40, 42, 118, 119, 120, 122, 123 and 124 are illustrated as smooth and planar, it is foreseen that these surfaces may be roughened or abraded to provide enhanced frictional contact between the retainer pieces 101 and 102 and the shank upper portion 8. Furthermore, the outer surfaces 104 and 105 of the retainer and articulation structure 12 that contact the substantially spherical seating surface 94 of the receiver may also be a high friction surface, such as a knurled surface.

The retainer part or piece 101 further includes end walls 132 and 133, extending from the outer surface 104 to the inner walls 118 and 120, respectively. The end walls 132 and 133 are disposed substantially perpendicular to the bottom surface 110. The retainer part 102 further includes end walls 134 and 135, extending from the outer surface 105 to the inner walls 122 and 124, respectively. The end walls 134 and 135 are disposed substantially perpendicular to the bottom surface 111. Each of the walls 132, 133, 134 and 135 include a top bevel 136. The retainer parts 101 and 102 are configured such that, when operationally disposed in the receiver 10, with the substantially spherical surfaces 104 and 105 in sliding frictional contact with the spherical seating surface 94, and with the bottom surfaces 110 and 111 seated on the annular seating surface 44 of the shank 4, the end walls 132 and 133 are in contact with the respective end walls 134 and 135, as illustrated in FIGS. 1 and 4. The bevels 136 providing clearance space for installing the retainer structure parts 101 and 102 about the capture structure 8 within the receiver 10 in a method of the invention described subsequently herein. It is foreseen that also in accordance with the invention, to provide additional clearance during installation, the parts 101 and 102 may be configured such that the end walls 132 and 133 are in spaced, substantially parallel relation with the respective end walls 134 and 135, when fully installed in the bone screw receiver 10.

With particular reference to FIGS. 1 and 9-11, the illustrated compression insert 14 is sized and shaped to be received by and downloaded into the receiver 10 at the upper opening 66. However, in other embodiments of the invention, the insert 14 may be sized for uploading or downloading into the receiver 10. In operation, the insert 14 is disposed between the rod 21 and the upper portion 8 of the bone screw shank 4 as illustrated for example in FIGS. 10 and 11. When the closure structure 18 presses upon the rod 21, the rod 21 operatively presses upon the insert 14 that in turn presses upon the shank top end surface 46, that in turn causes the shank upper portion 8 to press against the retainer pieces 12 that in turn press against the seating surface 94 of the receiver 10, resulting in ultimate frictional engagement and locking of the angular position of the bone screw shank 4 with respect to the receiver 10. The compression insert 14 has an operational central axis that is the same as the central axis B of the receiver 10.

The compression insert 14 has a central channel or through bore substantially defined by an inner cylindrical surface 141 coaxial with an inner partially spherical surface 142. The compression insert 14 through bore is sized and shaped to receive a driving tool (not shown) therethrough that engages the shank drive feature 52 when the shank body 6 is driven into bone. The surface 142 is sized and shaped to cooperate and ultimately frictionally engage the substantially spherical or domed surface 46 of the shank upper portion 8 such that the surface 142 initially slidingly and pivotally mates with the spherical surface 46. The surface 142 may include a roughening or surface finish to aid in frictional contact between the surface 142 and the surface 46, once a desired angle of articulation of the shank 4 with respect to the receiver 10 is reached.

The compression insert 14 also includes a pair of arms 144 with a U-shaped surface or saddle 146 formed therebetween. The saddle 146 defines a U-shaped channel that communicates with the bore defined by the cylindrical surface 141 and the spherical surface 142. The curved surface or saddle 146 is sized and shaped to closely receive the cylindrical rod 21 or other longitudinal connecting member. The saddle 146 extends from top surfaces 148 of the arms to a curved lower seat 150 located near a bottom surface 152 of the insert 14. The surface 152 slopes upwardly from and communicates with the inner spherical surface 142, the surface 152 allowing for clearance between the insert 14 and the retainer pieces 12 as best shown in FIG. 11. The height of the arms 144 can vary as can their thickness and the area for their top surfaces 148.

In operation, the lower seat 150 (as well as a substantial portion of a remainder of the saddle 146) frictionally engages an outer surface 22 of the rod 21. A base having an outer cylindrical surface 154 is disposed between the saddle 146 and the bottom surface 152. The cylindrical surface 154 also extends upwardly about the arms 144. Formed in the surface 154 and located centrally with respect to each arm 144 is a shallow groove or depression 156. Each illustrated groove 156 is substantially U-shaped and runs from the respective top surface 148 to a curved or flat bottom 158 located approximately centrally between the top surface 148 and the bottom surface 152. The grooves 156 are sized and shaped to cooperate with the tabs 80 of the receiver 10 as will be described in greater detail below. The grooves 156 may be of any shape and are preferably elongate, running parallel to a central axis of the insert 14 that is operationally coaxial with the axis B of the receiver 10, and have a width that receives the respective tab 80 within such groove. In the illustrated embodiment, the grooves or depressions 156 are substantially flat surfaces formed by planing the cylindrical surface 154. The compression or pressure insert 14 ultimately seats on the shank upper portion 8 and is disposed substantially in the upper cylindrical portion 92 of the cavity 90, with the tabs 80 holding the insert 14 in desired alignment with respect to the rod 21 as will be described in greater detail below. In operation, the insert 14 extends at least partially in the channel 64 such that the saddle 146 surface substantially contacts and engages the outer surface 22 of the rod 21 when such rod is placed in the receiver 10 and the closure structure or top 18 is tightened thereon.

The elongate rod or longitudinal connecting member 21 that is utilized with the assembly 1 can be any of a variety of implants utilized in reconstructive spinal surgery, but is typically a cylindrical, elongate structure having the outer substantially smooth, cylindrical surface 22 of uniform diameter. The rod 21 may be made from a variety of metals, metal alloys and deformable and less compressible plastics, including, but not limited to rods made of elastomeric, polyetheretherketone (PEEK) and other types of materials. The rod 21 is cradled by and directly or abutingly engages the insert 14 at the saddle 146, as shown in FIGS. 10 and 11 and is biased against the saddle 146 by pressure from the closure structure 18, consequently biasing the insert surface 142 against the shank upper portion top end surface 46, pressing the shank 4 downwardly in a direction toward the base 60 of the receiver 10 when the assembly 1 is fully assembled. The shank 4 and retainer structure pieces 12 are thereby locked or held in position relative to the receiver 10 by the rod 21 firmly pushing downward on the insert 14 that in turn pushes down on the shank upper surface 46.

With reference to FIGS. 1, 10 and 11, the closure structure or closure top 18 can be any of a variety of different types of closure structures for use in conjunction with the present invention with suitable mating structure on the upstanding arms 62. In the embodiment shown, the closure top 18 is rotatably received between the spaced arms 62, but could be a slide-in closure structure. The illustrated closure structure 18 is substantially cylindrical and includes an outer helically wound guide and advancement structure 162 in the form of a flange form that operably joins with the guide and advancement structure 72 disposed on the arms 62 of the receiver 10. The flange form utilized in accordance with the present invention may take a variety of forms, including those described in Applicant's U.S. Pat. No. 6,726,689, which is incorporated herein by reference. It is also foreseen that according to the invention the closure structure guide and advancement structure could alternatively be a buttress thread, a square thread, a reverse angle thread or other thread like or non-thread like helically wound advancement structure for operably guiding under rotation and advancing the closure structure 18 downward between the arms 62 and having such a nature as to resist splaying of the arms 62 when the closure structure 18 is advanced into the U-shaped channel 64. The illustrated closure structure 18 also includes a top surface 164 with an internal drive 166 in the form of an aperture that is illustrated as a hex drive, or may be, for example, a star-shaped internal drive such as that sold under the trademark TORX, or other internal drives such as slotted, tri-wing, spanner, two or more apertures of various shapes, and the like. A driving tool (not shown) sized and shaped for engagement with the internal drive 166 is used for both rotatable engagement and, if needed, disengagement of the closure 18 from the receiver arms 62. It is also foreseen that the closure structure 18 may alternatively include a break-off head designed to allow such a head to break from a base of the closure at a preselected torque, for example, 70 to 140 inch pounds. Such a closure structure would also include a base having an internal drive to be used for closure removal. A bottom surface 168 of the closure may be planar or include a point, points, a rim or roughening for engagement with the surface 22 of the rod 21. The closure top 18 may further include a cannulation through bore (not shown) extending along a central axis thereof and through the top and bottom surfaces thereof. Such a through bore provides a passage through the closure 18 interior for a length of wire (not shown) inserted therein to provide a guide for insertion of the closure top into the receiver arms 62.

Prior to the polyaxial bone screw assembly 1 being placed in use according to the invention, the retainer structure pieces 101 and 102 are typically first inserted or top-loaded into the receiver U-shaped channel 64 at the opening 66, as shown in FIG. 6, and then into the cavity 90 to ultimately dispose the structure pieces 12 adjacent to the inner surface 94 of the receiver 10. Alternatively, one of the retainer structure pieces 101 may be inserted or top-loaded into the channel 64 at the opening 66, while the other retainer structure piece 102, may inserted or bottom-loaded into the cavity 90 at the lower neck 96. Alternatively, both pieces 101 and 102 may be uploaded at the neck 96.

With reference to FIGS. 7 and 8, after the retainer pieces 101 and 102 are disposed in the cavity 90, the shank 4 is inserted or up-loaded into the receiver 10 at the neck 96. With particular reference to FIG. 8, the sloping surfaces 40 and 42 of the shank upper portion 8 come into contact with the sloping inner surfaces 118, 119, 120, 122, 123 and 124 of the respective retainer pieces 101 and 102. Initially all three components, the shank upper portion 8, and the pieces 101 and 102 may move upwardly into the cavity 90. As the shank upper portion 8 continues to move upwardly and into the cavity 90, the retainer structure pieces 101 and 102 pivot about edges thereof and then begin to move downwardly toward the base 60 until in operational alignment as shown in FIG. 9 with the bottom surfaces 110 and 111 abutting and seated upon the annular seating surface 44 of the shank 4. Once seated upon the annular surface 44, the retainer structure sloping surfaces 118, 119, 120, 122, 123 and 124 frictionally engage the capture structure side surfaces 40 and 42. Subsequent slight downward movement (directed away from the top opening 66) by the shank 4, as well as the frictionally engaged retainer pieces 101 and 102, seats the shank/retainer structure assembly in the receiver cavity 90, with the retainer outer spherical surfaces 104 and 105 in sliding engagement with the receiver seating surface 94. The retainer structure pieces 12, now fully seated in the receiver 10 are coaxially aligned with the shank upper portion. At this time, the shank upper portion 8, the retainer structure 12, the receiver seating surface 94 and the lower aperture or neck 96 cooperate to maintain the shank body 6 in pivotal and rotational relation with the receiver 10. Only the retainer structure 12 is in slidable engagement with the receiver spherical seating surface 94. Both the shank upper portion 8 and the threaded portion of the shank body 6 are in spaced relation with the receiver 10. An extent of rotation is shown in FIG. 11 where it is illustrated that the shank body 6 can be rotated through a substantial angular rotation relative to the receiver 10, both from side to side and from front to rear so as to substantially provide a universal or ball joint wherein the angle of rotation is only restricted by engagement of the neck of the shank body 6 with the restrictive neck 96 of the receiver 10.

Prior to the polyaxial bone screw assembly 1 being placed in use according to the invention the tabs 80 of the receiver 10 may be bent inwardly toward the axis B as shown in FIG. 11. This is accomplished by inserting an elongate tool (not shown) into each of the tooling apertures 74 and pressing the respective tab 80 inwardly toward the axis B until the tab end 84 is disposed at least partially within the upper cylindrical portion 92 of the cavity 90. In the illustrated embodiment, the insert 14 is top loaded through the opening 66 of the receiver 10 and the grooves 156 are aligned with the tabs 80. The tabs 80 are bent inwardly toward the axis B after the pressure insert 14 is located in the cylindrical portion 92 of the cavity 90. The tabs 80 are then pressed toward the axis B until the tabs 80 come into frictional engagement with surfaces 156 of the receiver 14. The tabs 80 press against the insert 14 at the grooves 156, allowing for some upward and downward adjustment of the insert 14. However, rotation of the insert 14 about the axis B is prohibited by the tabs 80 abutting against surfaces forming the grooves 156.

The retainer 12 and the attached shank upper portion 8 may then be manipulated into a substantially coaxial position with the insert 14 in readiness for bone implantation. The assembly 1 is typically screwed into a bone, such as a vertebra (not shown), by rotation of the shank 4 using a driving tool (not shown) that operably drives and rotates the shank 4 by engagement thereof with the drive feature 52.

The vertebra (not shown) may be pre-drilled to minimize stressing the bone and have a guide wire (not shown) inserted to provide a guide for the placement and angle of the shank 4 with respect to the vertebra. A further tap hole may be made using a tap with the guide wire as a guide. Then, the bone screw assembly 1 is threaded onto the guide wire utilizing the cannulation bore 54 by first threading the wire into the opening at the bottom 28 and then out of the top opening at the drive feature 52. The shank 4 is then driven into the vertebra using the wire as a placement guide. It is foreseen that the bone screw assemblies 1, the rod 21 (also having a central lumen in some embodiments) and the closure top 18 (also with a central bore) can be inserted in a percutaneous or minimally invasive surgical manner, utilizing guide wires.

With reference to FIG. 10, the rod 21 is eventually positioned in an open or percutaneous manner in cooperation with the at least two bone screw assemblies 1. Alignment of the rod surface 22 with the saddle 146 of the insert 14 is initially provided and then maintained by pressure placed at the insert grooves 156 by the tabs 80. The closure structure 18 is then inserted into and advanced between the arms 62 of each of the bone screw assemblies 1. The closure structure 18 is rotated, using a tool engaged with the inner drive 166 until a selected pressure is reached at which point the rod 21 engages the saddle 146 and the rod is urged toward, but not in contact with the lower seat of the receiver 10 that defines the U-shaped channel 64. For example, about 80 to about 120 inch pounds pressure may be required for fixing the bone screw shank 6 with respect to the receiver 10.

As the closure structure 18 rotates and moves downwardly into the respective receiver 10, the bottom surface 168 presses against the rod surface 22, biasing the rod into engagement with the compression insert 14 that operably produces a frictional engagement between the insert surface 142 and the shank surface 46 and also urges the shank upper portion 8 toward the retainer 12 and, in turn, the structure 12 in a direction toward the base 60 of the receiver 10, so as to frictionally seat the spherical surfaces 104 and 105 against the internal spherical seating surface 94 of the receiver 10, also fixing the shank 4 and the retainer 12 in a selected, rigid position relative to the receiver 10. At this time it is also possible for the retainer 12 to expand somewhat for an even tighter fit in the receiver cavity lower seat 94.

If removal of the rod 21 from any of the bone screw assemblies 1 is necessary, or if it is desired to release the rod 21 at a particular location, disassembly is accomplished by using the driving tool (not shown) that mates with the internal drive 166 on the closure structure 18 to rotate and remove the closure structure 18 from the cooperating receiver 10. Disassembly is then accomplished in reverse order to the procedure described previously herein for assembly.

It is to be understood that while certain forms of the present invention have been illustrated and described herein, it is not to be limited to the specific forms or arrangement of parts described and shown.

What is claimed and desired to be secured by Letters Patent is as follows:

1. A pivotal bone anchor assembly for securing an elongate rod to a bone, the bone anchor assembly comprising:
    a receiver comprising a base defining a first cavity and a pair of arms extending upwardly from the base to define an open channel for receiving the rod, the first cavity communicating with the open channel and with a bottom surface of the receiver through a bottom opening;
    a shank having a lower attachment portion for attachment to the bone and an integral upper capture portion up-loadable into the first cavity through the receiver bottom opening; and
    a two-piece retainer structure comprising two separable retainer parts, each retainer part being positionable within the receiver first cavity prior to the shank to together define a second cavity having inner mating surfaces operable to engage an outer surface of the shank upper capture portion so as to hold the upper capture portion within the receiver and in spaced relation from an inner retainer engaging surface of the first cavity,
    wherein the two retainer parts at least partially move away from each other upon insertion of the shank upper capture portion through the bottom opening to capture the shank upper capture portion within the receiver first cavity with the shank lower attachment portion extending distally through the receiver bottom opening.

2. The bone anchor assembly of claim 1, wherein the shank is movable polyaxially with respect to the receiver.

3. The bone anchor assembly of claim 1, wherein at least one of the first cavity inner retainer engaging surface and the second cavity inner mating surfaces is conical in shape.

4. The bone anchor assembly of claim 1, wherein the shank upper capture portion further comprises an external spherical surface.

5. The bone anchor assembly of claim 1, wherein the receiver first cavity inner retainer engaging surface decreases in diameter toward the bottom opening.

6. The bone anchor assembly of claim 5, wherein each retainer part has a top surface, a bottom surface, and an outer surface that decreases in diameter in the direction from the top surface to the bottom surface.

7. The bone anchor assembly of claim 1, wherein a force directed downwardly onto the two-piece retainer structure in operable engagement with the shank upper capture portion causes outer surfaces of the retainer parts to become frictionally engaged with the first cavity inner retainer engaging surface to lock the angular orientation of the shank with respect to the receiver.

8. The bone anchor assembly of claim 7, wherein the retainer pieces outer surfaces are slidably engageable with the first cavity inner retainer engaging surface after capturing the shank upper capture portion within the receiver first cavity and prior to locking the angular orientation of the shank with respect to the receiver.

9. The bone anchor assembly of claim 1, further comprising an insert disposed within the receiver between the two-piece retainer structure and the elongate rod and having a curved upper saddle surface operable to receive the elongate rod, the insert being configured to transfer a downwardly-directed force from the elongate rod to the two-piece retainer structure.

10. The bone anchor assembly of claim 1, wherein the retainer parts pivot and move apart with respect to each other within the receiver first cavity so as to capture the shank therein.

11. The bone anchor assembly of claim 1, wherein the retainer parts move toward each other to form the second cavity having the inner mating surfaces that are operable to engage the outer surface of the shank upper capture portion.

12. The bone anchor assembly of claim 1, wherein each retainer part further comprises end walls in spaced parallel relation with the respective end walls of the other retainer part when the two-piece retainer structure is in operable engagement with the shank upper capture portion within the receiver first cavity.

* * * * *